(12) United States Patent
Blake et al.

(10) Patent No.: US 10,228,085 B2
(45) Date of Patent: Mar. 12, 2019

(54) FLUID CONNECTOR HAVING INTEGRATED PIPE CLAMPING

(71) Applicant: SARTORIUS STEDIM FMT SAS, Aubagne (FR)

(72) Inventors: Florian Blake, Hyeres (FR); Jeremy Gibelin, Le Beausset (FR); Isabelle Gay, Peypin (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 493 days.

(21) Appl. No.: 14/392,169

(22) PCT Filed: Jun. 26, 2014

(86) PCT No.: PCT/FR2014/051623
§ 371 (c)(1),
(2) Date: Dec. 23, 2015

(87) PCT Pub. No.: WO2014/207392
PCT Pub. Date: Dec. 31, 2014

(65) Prior Publication Data
US 2016/0178101 A1 Jun. 23, 2016

(30) Foreign Application Priority Data
Jun. 28, 2013 (FR) .................... 13 56355

(51) Int. Cl.
*F16L 33/22* (2006.01)
*A61M 39/10* (2006.01)
(Continued)

(52) U.S. Cl.
CPC .......... *F16L 33/225* (2013.01); *A61J 1/2048* (2015.05); *A61M 39/1011* (2013.01);
(Continued)

(58) Field of Classification Search
CPC .... F16L 33/221; F16L 33/225; F16L 33/2073
See application file for complete search history.

(56) References Cited

U.S. PATENT DOCUMENTS

| 1,390,564 A | * | 9/1921 | Knorr | F16L 33/221 |
| | | | | 285/243 |
| 3,222,091 A | * | 12/1965 | Marshall | F16L 33/222 |
| | | | | 285/243 |

(Continued)

FOREIGN PATENT DOCUMENTS

| DE | 2220919 A1 * | 11/1972 | .............. F16L 37/05 |
| DE | 86 10 238 U1 | 8/1986 | |

(Continued)

OTHER PUBLICATIONS

International Search Report, dated Oct. 24, 2014, from corresponding PCT application.

*Primary Examiner* — James M Hewitt, II
(74) *Attorney, Agent, or Firm* — Young & Thompson

(57) ABSTRACT

A coupling device for sealingly coupling a first wall defining a flexible pipe (11) to a tubular nozzle (9) of a connector (1) in a biopharmaceutical assembly, the coupling device including the connector (1) including the tubular nozzle (9), on which one end of the pipe can be inserted along an axis A, a plurality of flexible tabs (3) extending from an intermediate area (7) of the coupling body toward the free end (1a) of the nozzle, an abutment clamp (16), a connection interface (6), a separate ring (2), axially movable between an inoperative position and an operative position, for covering the flexible tabs (3) such as to push same radially inward in order to press the pipe onto the nozzle in the operative position, the tabs extending substantially parallel to the axis (A) when the ring (2) is in the operative position.

20 Claims, 2 Drawing Sheets

(51) Int. Cl.
*A61M 39/12* (2006.01)
*F16L 37/098* (2006.01)
*A61J 1/20* (2006.01)
*A61J 1/14* (2006.01)

(52) U.S. Cl.
CPC ........... *A61M 39/12* (2013.01); *F16L 33/221* (2013.01); *F16L 37/0987* (2013.01); *A61J 1/1481* (2015.05); *A61M 2039/1027* (2013.01); *F16L 2201/44* (2013.01)

(56) References Cited

U.S. PATENT DOCUMENTS

| | | | | |
|---|---|---|---|---|
| 4,212,487 A | * | 7/1980 | Jones | F16L 33/225 |
| | | | | 285/243 |
| 4,564,222 A | * | 1/1986 | Loker | F16L 33/18 |
| | | | | 285/243 |

FOREIGN PATENT DOCUMENTS

| | | | | |
|---|---|---|---|---|
| DE | 19512986 C1 | * | 1/1997 | ............ F16L 33/225 |
| DE | 103 55 463 A1 | | 6/2005 | |
| DE | 10 2005 007217 B3 | | 5/2006 | |
| DE | 102005007217 B3 | * | 5/2006 | .......... F16L 25/0045 |
| DE | 102014100028 A1 | * | 7/2015 | ............ F16L 13/146 |
| EP | 0 091 773 A2 | | 10/1983 | |
| EP | 1288554 A1 | * | 3/2003 | ............ F16L 13/146 |
| FR | 2 605 709 A1 | | 4/1988 | |
| JP | 5111212 B2 | * | 1/2013 | ............ F16L 33/225 |
| WO | 2005/073613 A1 | | 8/2005 | |

\* cited by examiner

FLUID CONNECTOR HAVING INTEGRATED PIPE CLAMPING

BACKGROUND OF THE INVENTION

Field of the Invention

The invention relates to fluid connections, in particular fluid connections to couple a fluid-conveying pipe to another pipe or to a container, in the field of biopharmaceutical applications.

Specifically, the tubes or pipes used in the biopharmaceutical field are flexible or highly flexible pipes which are used to convey various biopharmaceutical substances, most often with the aseptic precautions required. In biopharmaceutical applications, this type of flexible pipe allows the circulation, passage, and communication of a fluid such as a biopharmaceutical fluid, and can either be connected to a similar flexible pipe or to a vessel or container. Said vessel or container may be rigid or flexible, and may be a bag, or a filter or filter cartridge.

A pipe of the invention, usually of circular cross-section, is typically made of a plastic such as silicone, thermoplastic elastomers (TPE), or PVC, although this list is not limiting. It has a certain general stability, and simultaneously both a certain overall flexibility and a certain local flexibility, which allows crimping the pipe or substantially deforming it radially when sufficient force is applied.

In a typical embodiment, for example, the pipe has an outer diameter between 8 mm and 30 mm for example, with the thickness depending on the material, the diameter, and the applications.

In the prior art, in order to couple such a flexible pipe, it is slipped over a tubular nozzle, whereupon a pipe clamp is placed around the pipe and the clamp is then tightened. The tightened clamp thus exerts a radial inward pressure to retain the flexible pipe on the nozzle, on the one hand to ensure a good seal between pipe and nozzle and on the other hand to prevent the pipe from detaching from the nozzle when pulled.

For such pipe clamps, a plastic clamp can be used for example, of polyamide for example such as Rilsan®. This type of plastic clamp, also sometimes called Serflex®, comprises a system of notches on a strip cooperating with a locking hook arranged in the head, such that the tightening is not reversible. In other words, after the strip is inserted into the head to form a loop, the strip is pulled to reduce the diameter of the loop and tighten the clamp; any return movement is prevented by the engagement of the hook in one of the notches of the strip. After tightening, to prevent the strip from projecting too far beyond the diameter of the clamp loop, the free portion of the strip is cut off close to the head of the clamp. The undetached remaining portion of the strip often has a sharp edge which can cut.

As an alternative to the plastic clamp, a metal clamp can be used which is in the form of a preformed ring having one or two "ears" projecting outward beyond the general shape of the ring of the clamp; this type of clamp is sometimes referred to as an Oetiker® clamp. After placement of the clamp on the pipe to be retained, a tool is used to crimp the ear (or ears) of the clamp which causes a permanent deformation and thus a narrowing of the major diameter of the ring and as a result tightens the clamp on the pipe. This type of clamping with a metal ring is particularly robust and reliable. However, at the point where the ear was crimped by the tool, there may be a burr or roughness which forms a sharp edge that can be damaging.

It should be noted, however, that it is also possible to use crimp-on earless metal clamps.

Whether plastic or metal, once such clamps are installed in biopharmaceutical assemblies, these assemblies may need to be transported or moved and therefore there is therefore is a risk of damage by the damaging parts of these clamps to other elements of the biopharmaceutical assembly, particularly the flexible bags or flexible pipes, which can cause a leakage or loss of sterilization that is detrimental to biopharmaceutical application.

In addition, these clamps are easy to access (and thus can be removed) and do not allow guaranteeing a satisfactory image or aesthetics.

Moreover, the above clamp-based solutions are imperfect in their seal between the flexible pipe and the tubular nozzle. In fact, the seal at the ear of the metal collar or at the head of the plastic collar has a discontinuity in the radial pressure, and therefore can be improved.

In addition, such clamps are tightened by a manual operation; the reliability of such an operation is lower than that of an automated operation.

There is therefore a need to propose an improvement intended to at least partially overcome one of the above drawbacks of the known prior art.

BRIEF SUMMARY OF THE INVENTION

According to a first aspect, the invention relates to a coupling device adapted and intended for coupling a first wall defining a first fluid space, in the form of a flexible pipe, to a second wall formed by a tubular nozzle of a connector, in a biopharmaceutical assembly, to enable establishing a seal between the first wall and the second wall formed by the tubular nozzle, the coupling device comprising:
  said connector with:
    said tubular nozzle, onto which one end of the pipe can be inserted along an axis A, from a first end of the nozzle until it reaches a stop area for the pipe,
    a plurality of flexible tabs extending from an intermediate area of the connector body toward the free end of the nozzle, the flexible tabs being distributed all around the circumference of the nozzle,
    a connection interface arranged opposite the tubular nozzle,
  a separate ring which is axially movable between an inoperative position and an operative position, adapted and intended for covering the flexible tabs so as to force them radially inward in a manner that presses the pipe onto the nozzle in said operative position, thereby creating a radial sealing contact between the pipe and the tubular nozzle, the flexible tabs extending substantially parallel to the axis A when the ring is in the operative position, the separate ring being moved in the direction of the connector body to transition from the inoperative position to the operative position.

The clamping of the pipe is thus particularly effective. In particular, the clamping is well-distributed and uniform over the entire circumference around the pipe and along a certain axial length. In addition, it is not necessary to rotate the ring: a movement of axial displacement is sufficient and the proper operative position can easily be checked visually.

In addition, automation of the insertion of the pipe and ring to form a coupling device can be considered, providing the reliability of an automated operation.

This does not exclude manual assembly of the coupling device, however, and this can advantageously be done without tools.

Advantageously, the flexible tabs are formed integrally from the intermediate area of the body, and when at rest they lie in a cone shape which opens toward the end of the nozzle, such that the end of the flexible pipe can be inserted onto the nozzle when beginning assembly without the flexible tabs posing an obstacle. In addition, this has the advantage of facilitating unmolding during connector production.

In one embodiment, the free ends of the flexible tabs comprise chamfers for the ring. The ring thus acts on the chamfers at the beginning of the ring insertion movement, which presses the flexible tabs radially inward.

In one embodiment, the ring comprises a conical flared region that slides externally over the free ends of the flexible tabs. The insertion force exerted on the ring by an operator or a machine tool thus exerts a force having an inward radial component so that the flexible tabs are pressed inward.

In one embodiment, the connector comprises a collar and the collar forms a stop to end the axial insertion movement of the ring; this provides a simple and reliable index for the end of the insertion movement.

In one embodiment, the flexible tabs comprise at least one tooth on the radially inner face, such that the pressure on the pipe is greater at this tooth; this constitutes an anchor intended to prevent withdrawal of the pipe even if a pulling force is exerted on the pipe.

In one embodiment, the nozzle comprises at least one notch that is axially offset relative to the tooth, thereby strengthening said anchoring of the pipe on the nozzle.

In one embodiment, in the operative position of the ring, the tabs are sandwiched between the ring and the pipe for a length representing more than half of the axial length of the ring, and preferably for a length greater than the inside diameter of the nozzle. This provides a large contact surface between the pipe and the nozzle, which helps with retention and sealing.

In one embodiment, in the operative position of the ring, the flexible tabs are adjacent to one another in the circumferential direction. The radial pressure of the flexible tabs is thus exerted along the entire periphery of the pipe.

In one embodiment, the first connector forms a male interface adapted to be received in a second connector forming a female interface; this represents a fluid interface solution that is particularly simple for connecting several types of pipe to the entity integral with the second connector.

The first connector comprises an attachment disc configured to be attached directly to a filter or bag type of container; this allows easily coupling the pipe directly to a container.

In one embodiment, the ring comprises a radially external shoulder to facilitate the movement from the inoperative position to the operative position; this allows automating the ring insertion. It also makes it possible to consider a tool-free movement of the ring and therefore a completely manual assembly of the coupling.

In one embodiment, the ring comprises an annular rib received in a notch provided on the outer face of each flexible tab; this provides a solution for locking the position of the ring in its operative position, which occupies a limited footprint radially and axially.

In one embodiment, the annular rib has a cross-section with a tip pointing towards the rear of the pipe; this provides a harpoon shape that is particularly effective for locking the operative position.

In one embodiment, the ring comprises a fastening clip configured to clip the ring onto the collar in the operative position; this represents an alternative solution for axial retention of the ring in its operative position.

In one embodiment, the first connector or the ring may further comprise an identifier such as a barcode or RFID tag or color code. It is thus easy to access information concerning the flexible pouch and/or the biopharmaceutical product contained therein, in particular in order to contribute to the traceability function.

According to a second aspect, the invention relates to a method for forming a coupling device intended for sealingly coupling a flexible pipe to a tubular nozzle of a connector, the method comprising the steps of:

/a/ providing a connector of molded plastic, said connector comprising:
  a tubular nozzle, onto which one end of a flexible pipe can be inserted along an axis A, with a stop area to end the insertion path of the pipe,
  a plurality of flexible tabs extending from an intermediate area of the connector body toward the free end of the nozzle,
  a connection interface arranged opposite the tubular nozzle;

/b/ providing a separate ring, and placing it in an inoperative position on the pipe;

/c/ inserting the pipe onto the tubular nozzle until the stop area is reached,

/d/ moving the ring axially from the inoperative position into an operative position which is adapted and intended for covering the flexible tabs so as to force them radially inward in a manner that presses the pipe onto the nozzle in said operative position, the tabs extending substantially parallel to the axis (A) when the ring is in the operative position.

In this manner, the coupling device is formed by a solely axial movement of the ring, which can be obtained by a manual tool-free operation or by an automated operation.

According to a third aspect, the invention relates to a biopharmaceutical assembly comprising a fluid-connection device as described above.

According to a fourth aspect, the invention also provides a kit of parts comprising the first connector and the ring, which are described above, with at least one flexible pipe portion.

In addition, the invention relates to an assembly of the above parts into an assembled state with the ring in the operative position clamping the pipe onto the nozzle.

BRIEF DESCRIPTION OF THE DRAWINGS

The drawings in the figures are now briefly described.

DETAILED DESCRIPTION OF THE PREFERRED EMBODIMENTS

Figure 1:
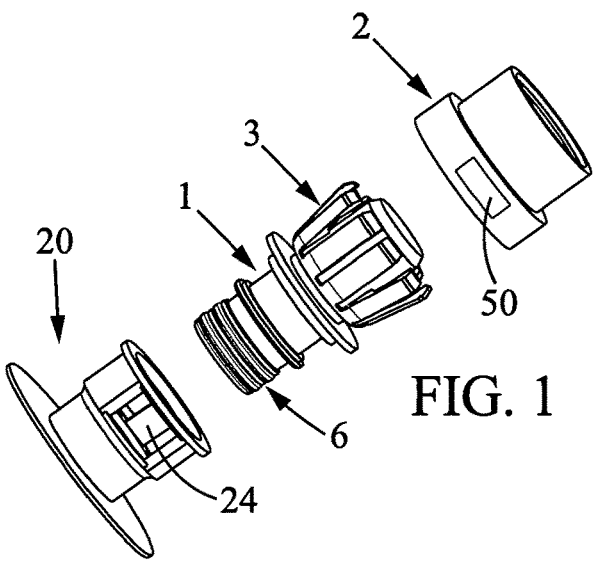
FIG. 1 is an exploded view of a coupling device according to the present invention.

Below is a detailed presentation of an embodiment of the invention, accompanied by examples and with reference to the drawings.

In the example illustrated in FIGS. 1-3, a flexible pipe 11 is connected to a first connector 1 in a fluidtight manner, by means of a separate ring 2 which will be further described below. The first connector is intended to be coupled to a second connector 20 to form a fluid connection between two fluid spaces.

The flexible pipe 11 can be generally defined as a first wall 11 defining a first fluid space 71. The outer diameter of the flexible pipe 11 at rest is denoted D2.

The first connector 1 is made of synthetic material, more specifically it can be obtained by molding a plastic material, for example polypropylene, polyethylene, polycarbonate, polysulfone.

The first connector 1 comprises a tubular nozzle 9 at one 1a of its ends, and an interface 6 for coupling with a second connector 20 at the other of its ends. The first connector 1 further comprises an intermediate portion 7 which will be further described below.

The tubular nozzle 9 is symmetrical about the axis A and forms a second wall. One will note that the inner diameter D1 of the tubular nozzle 9 is substantially close to the inner diameter of the flexible pipe 11 at rest, but it should be noted that the nozzle is adapted to receive a range of pipes of substantially different diameters around D1, said pipe easily deforming radially at insertion.

When the flexible pipe 11 is threaded onto the tubular nozzle 9, the pipe is deformed radially outward by the ramp formed by the chamfered edge, and then as it is progressively inserted in the direction of arrow F it conforms to the outside diameter of the nozzle. Insertion of the flexible pipe can continue until the front end of the pipe 11a comes to bear against a stop area 30 which will be described below (see FIG. 3).

The nozzle 9 may have an outer surface in the form of a smooth cylinder, it may or may not comprise one or more annular notches 19, which in the example shown each have a slight ramp on the side of the flexible pipe to be inserted and a shoulder on the opposite side. The tubular nozzle may comprise a different number of notches, possibly even one notch or no notch.

In the example shown, the coupling interface 6 is a male interface that is intended for insertion into a female interface of the second connector 20. Of course, the reverse would be possible, meaning a male interface into the second connector and a female interface into the first connector, or possibly even a genderless interface.

In the example shown, the male interface 6 of the first connector is generally cylindrical about the axis A, with one or two outer grooves intended for receiving one or two O-rings 35 to establish the seal.

The intermediate portion 7 comprises a first collar 16 in the form of a disc, having a diameter larger than D2, this first collar serving as a stop for the insertion of the ring, and a second collar 14, also disc-shaped but smaller, its usefulness to be revealed further below.

Advantageously, the first connector 1 comprises a plurality of flexible tabs 3, numbering from 4 to 16, distributed all around the circumference of the nozzle. Each of the flexible tabs 3 comprises a fixed base 30 which extends from the intermediate portion 7 near the base of the first collar 16. This fixed base 30 forms a stop for the front end 11a of the pipe when the pipe is inserted onto the nozzle 9. Each flexible tab 3 further comprises a main arm 34 connected by a flexible elbow 37 to the fixed base 30, said main arm extending to a free end 32. The length L1 of the main arm 34 is greater than the inside diameter D1 of the pipe, and may even be greater than the outside diameter D2 of the pipe.

On the inner face of the main arm, each flexible tab comprises at least one tooth 31 intended to press into the outer surface of the pipe as will be further described below. There could be more than one tooth, for example another one near the free end 32. The tooth provides substantial penetration because the material of the flexible pipe is not as hard as the material of the flexible tabs.

The free end 32 comprises a chamfer 33 on its outer face to slide along the ring 2 and a groove 38 whose purpose will be seen below.

The separate ring 2 is as an annular symmetrical part of a harder plastic than that of the first connector, for example polyamide, PBT, ABS, or some other similar plastic material. The ring 2 comprises a first annular portion 23 of inner diameter D3, and a second annular portion 27 of a larger diameter facing towards the front of the connector. A flared conical region 29 is arranged radially internal to the second cylindrical portion, adjacent to its connection with the first cylindrical portion.

In addition, there is a radially external shoulder 26 between the first cylindrical portion and the second cylindrical portion. This shoulder 26 can serve as a bearing surface for the use of an automation tool; it also serves as a grasping surface when the ring is inserted manually by a user's fingers.

The ring 2 is placed on standby (in an inoperative position) at the back of the pipe prior to its assembly onto the first connector 1.

The method for assembling such a coupling device is presented below:

/a/ a connector 1 of molded plastic is provided, said connector comprising said tubular nozzle 9 adapted to receive said flexible pipe, /b/ the separate ring 2 is placed in an inoperative position on the pipe, /c/ the pipe 11 is inserted onto the tubular nozzle 9 along an axis A until it reaches the stop area 30, /d/ the ring 2 is moved from the inoperative position into an operative position where it abuts against the first collar 16.

One will note that in the solution illustrated, the ring 2 is moved in the direction of the connector body in order to transition from the inoperative position to the operative position; in other words the ring is moved from the rear of the pipe toward the front end of the pipe, in the same direction F as the flexible pipe insertion movement.

We will now describe step /d/ in more detail. During the movement of inserting the ring 2 as indicated by arrow F, the first flared conical region 29 comes alongside the chamfers 33 of the free end 32 of the flexible tabs, which starts a tightening movement toward the center of the axis of said flexible tabs.

As the movement continues, the ring 2, in particular its annular portion 23, progressively covers the entire length of the main arm 34 of each flexible tab, so as to completely cover the flexible tabs 3 and force them radially inward, which presses the pipe 11 against the nozzle 9.

According to one advantageous aspect, the tabs extend substantially parallel to the axis when in the operative position. The nozzle 9 and the flexible tabs 3 sandwich the pipe 11 along length L1, which is greater than D1. In a variant (not shown), the length L1 may be greater than the outer diameter D2 of the pipe.

Advantageously, the flexible tabs 3 are therefore forced radially inward which presses the pipe 11 against the nozzle 9 in said operative position, thereby creating a radial sealing contact between the pipe 11 and the tubular nozzle 9.

In a variant (not represented), the flexible tabs 3 could be longer and protrude beyond the end 1a of the nozzle 9.

At the end of the axial insertion movement, a front shoulder 22 of the ring abuts against the collar 16.

It should be noted here that the insertion movement does not require rotating the ring. However, if the ring is rotated during the insertion movement this does not change its radial effect on the flexible tabs.

The simplicity of this manual or automated insertion provides an improvement in the reliability of the assembly of the interface.

According to one optional aspect, in the operative position reached when the ring 2 is in abutment against the collar 16, an inward- and preferably rearward-facing annular rib 28 is received in a complementary notch 38 (or groove) provided on the rear outer face of the main arm 34 of each flexible tab 3. The notch or groove 38 is arranged at the beginning of the chamfer in the example illustrated, but could be located elsewhere.

Figure 3:
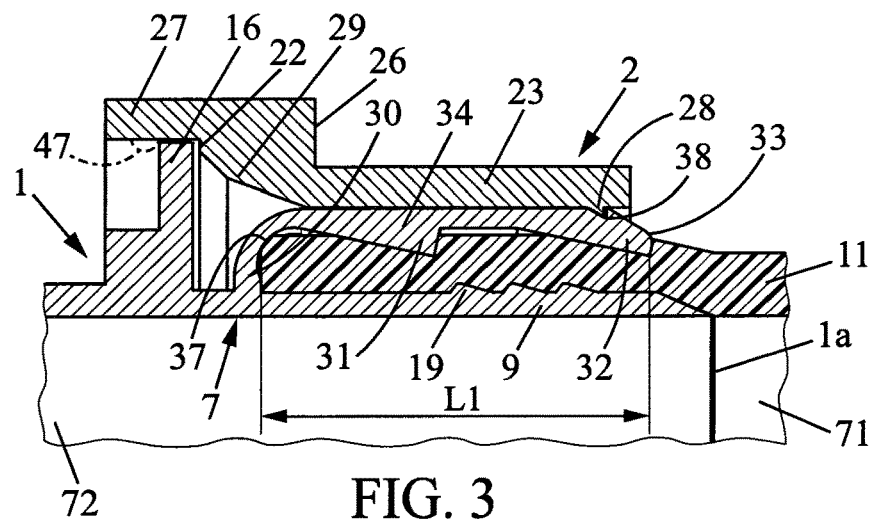
FIG. 3 is a more detailed axial sectional view of the coupling device of FIG. 1, in the coupled position.

According to an optional alternative aspect to the above solution, there could be one or more locking clip(s) 47 (or fastening clip) on the front part of the front annular portion 27 of the ring, which cooperates with said front shoulder 22 to snap-fit the ring 2 to the collar 16 when the ring is in the operative position (see FIG. 3).

According to one optional aspect, locking tongues 24 may be provided in the body of the second connector 20. These locking tongues 24, of which there are two in the example illustrated, are flexible, are moved apart when the second collar 14 reaches their free end, and then return inward to be positioned against a withdrawal-preventing abutment on the rear of the second collar 14. It is then impossible to reverse the movement, meaning to withdraw the first connector from the second connector, without first somehow eliminating the locking tongues 24.

Figure 2:
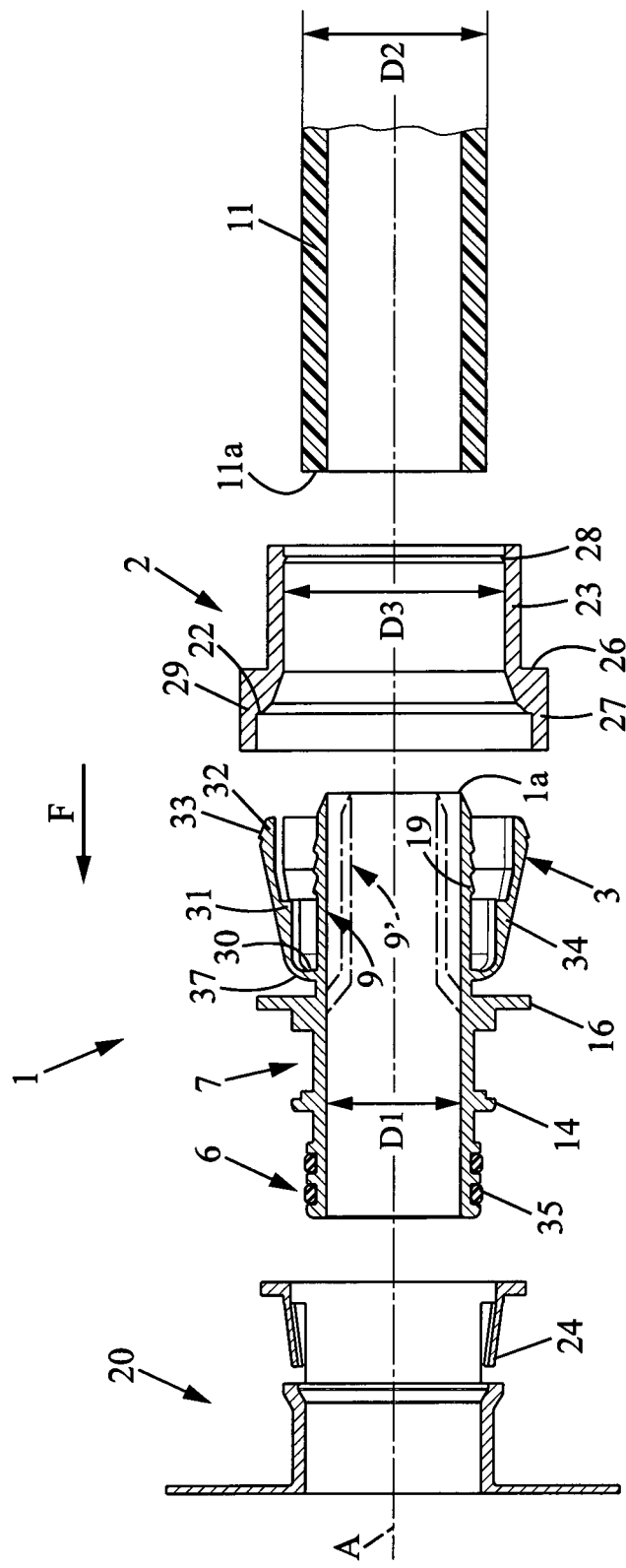
FIG. 2 is an axial sectional view of the coupling device of FIG. 1, in the separated position.

It should also be noted that the male interface 6 may be of a standard dimension for many types of diameters of the pipe 11 and nozzle 9,9' (see FIG. 2). In this manner there can be diverse diameters for the nozzle of the first connector, and several types of pipe of different diameters can interface with one type of second connector 20.

Figure 4:
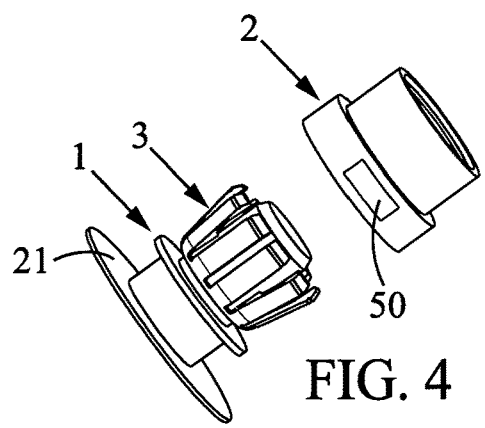
FIG. 4 is similar to FIG. 1 and shows a variant of the coupling device.

In the variant embodiment shown in FIG. 4, the connector 1 forms a socket for interfacing with a flexible or rigid bag, with no concept of a male or female interface. The coupling device then allows reliably coupling a flexible pipe directly to a bag, by means of a relatively wide annular attachment disc 21 which is attached by welding to the bag or to a wall of a filter cartridge.

In addition, an optional feature is provided that is compatible with all variants mentioned above: this is the integration of an identifier 50, such as a barcode, or an electronic tag for example an RFID tag, or a color code. Preferably, this identifier is provided on the ring 2, but in the case of the RFID tag could be provided on the first connector 1, accessible by transponder reading even after insertion of the ring 2 is complete.

It should be noted that the second connector 20 can interface with a second flexible pipe or a filter instead of having a disc for attachment to a bag as shown in FIG. 1.

The invention claimed is:

1. A coupling device adapted and intended for coupling a first wall defining a first fluid space, in the form of a flexible pipe, to a second wall formed by a tubular nozzle of a connector, in a biopharmaceutical assembly, to enable establishing a seal between the first wall and the second wall formed by the tubular nozzle, the coupling device comprising: said connector with:
said tubular nozzle, onto which one end of the pipe can be inserted along an axis A, from a first end of the nozzle until it reaches a stop area for the pipe,
a plurality of flexible tabs extending from an intermediate area of the connector body toward the free end of the nozzle, the flexible tabs being distributed all around the circumference of the nozzle,
a connection interface arranged opposite the tubular nozzle,
a separate ring which is axially movable between an inoperative position and an operative position, adapted and intended for covering the flexible tabs so as to force them radially inward in a manner that presses the pipe onto the nozzle in said operative position, thereby creating a radial sealing contact between the pipe and the tubular nozzle,
the tabs extending substantially parallel to the axis when the ring is in the operative position,
wherein the separate ring is moved in the direction of the connector body to transition from the inoperative position to the operative position,
wherein the flexible tabs are formed integrally from the intermediate area of the body, and when at rest they lie in a cone which opens towards the end of the nozzle, such that the end of the flexible pipe can be inserted onto the nozzle without the flexible tabs posing an obstacle, and
wherein said flexible pipe has a smooth wall.

2. The coupling device according to claim 1, wherein the free ends of the flexible tabs comprise chamfers for the ring.

3. The coupling device according to claim 1, wherein the ring comprises a conical flared region which slides over the free ends of the flexible tabs.

4. The coupling device according to claim 1, wherein the connector comprises a collar and the collar forms a stop to end the axial insertion movement of the ring.

5. The coupling device according to claim 1, wherein the flexible tabs comprise at least one tooth on the radially inner face, such that the pressure on the pipe is greater at this tooth.

6. The coupling device according to claim 5, wherein the nozzle comprises a notch that is axially offset relative to the tooth.

7. The coupling device according to claim 1, wherein, in the operative position of the ring, the tabs are sandwiched between the ring and the pipe for a length representing more than half of the axial length of the ring.

8. The coupling device according to claim 7, wherein, in the operative position of the ring, the tabs are sandwiched between the ring and the pipe for a length greater than the inside diameter of the nozzle.

9. The coupling device according to claim 1, wherein, in the operative position of the ring, the flexible tabs are adjacent to one another in the circumferential direction.

10. The coupling device according to claim 1, wherein the first connector forms a male interface adapted to be received in a second connector forming a female interface.

11. The coupling device according to claim 1, wherein the first connector comprises an attachment disc configured to be attached directly to a filter or bag type of container.

12. The coupling device according to claim 1, wherein the ring comprises a radially external shoulder to facilitate the movement from the inoperative position to the operative position.

13. The coupling device according to claim 1, wherein the ring comprises an annular rib received in a notch provided on the outer face of each flexible tab.

14. The coupling device according to claim 13, wherein the annular rib has a cross-section with a tip pointing towards the rear of the pipe.

15. The coupling device according to claim 1, wherein the ring comprises a fastening clip configured to clip the ring onto the collar in the operative position.

16. The coupling device according to claim 1, wherein the first connector or the ring further comprises an identifier.

17. A Biopharmaceutical assembly comprising a fluid-connection device according to claim 1.

18. A Method for forming a coupling device intended for sealingly coupling a flexible pipe for biopharmaceutical fluid to a tubular nozzle of a connector, said flexible pipe having a smooth wall, the method comprising the steps of:
/a/ providing a connector of molded plastic, said connector comprising:
    a tubular nozzle, onto which one end of a flexible pipe can be inserted along an axis A, with a stop area to end the insertion path of the pipe,
    a plurality of flexible tabs extending from an intermediate area of the connector body toward the free end of the nozzle, the flexible tabs being distributed all around the circumference of the nozzle, and formed integrally from the intermediate area of the body, and when at rest extending in a cone which opens toward the end of the nozzle,
    a connection interface arranged opposite the tubular nozzle,
/b/ providing a separate ring, and placing the separate ring in an inoperative position at the rear of the pipe,
/c/ inserting the pipe onto the tubular nozzle until the stop area is reached,
/d/ moving the ring axially from the inoperative position toward the connector body into an operative position which is adapted and intended for covering the flexible tabs so as to force them radially inward in a manner that presses the pipe onto the nozzle in said operative position, the tabs extending substantially parallel to the axis when the ring is in the operative position.

19. A biopharmaceutical assembly comprising:
a flexible pipe, the flexible pipe being comprised of a first wall having an outer diameter, a circular cross-section with a smooth internal wall surface, the first wall having a fixed thickness and a fixed interior diameter, an interior space defined by the first wall of the flexible pipe defining a first fluid space;
a first connector having a first end with a tubular nozzle and an opposite, second end with a connection interface, and an intermediate portion located between the first and second ends, the first end including i) plural flexible tabs that each terminate at a free end, and ii) a tubular nozzle having a threaded exterior surface and a ramp formed by a chamfered edge, the tubular nozzle being symmetrical about an axis (A) and being located interior to flexible tabs, the intermediate portion including a stop area connected to the flexible tabs such that the flexible tabs extend from the intermediate area around toward a free end of the nozzle, the flexible tabs being distributed all around a circumference of the nozzle, the flexible tabs at rest forming a cone which opens towards the end of the nozzle and allowing insertion of the end of the flexible pipe onto the threaded exterior surface of the nozzle without the flexible tabs posing an obstacle;
a ring, the ring being axially movable between an inoperative position and an operative position for covering the flexible tabs so as to force the flexible tabs radially to press the flexible pipe onto the nozzle in said operative position, thereby creating a radial sealing contact between the flexible pipe and the tubular nozzle,
wherein, with the ring in the operative position, the flexible tabs extend parallel to the axis, and the flexible pipe has a deformed end sealingly connected to the first connector in a fluid-tight manner, the flexible pipe being threaded onto the threaded exterior surface of the tubular nozzle, the end of the flexible pipe being deformed radially outward at the ramp at the chamfered edge, the flexible pipe conforming to an outside diameter of the nozzle, a distal end of the flexible pipe bearing against the stop area of the intermediate portion; and
a second connector sealingly connected to the connection interface of the first connector, the second connector configured for connection to a second fluid space with a fluid connection extending between the first and second fluid spaces.

20. The combination of claim 19, wherein,
the flexible pipe is plastic pipe,
the first connector is a plastic connector,
the ring is a plastic ring, the plastic of the ring being harder that the plastic of the first connector, and
the flexible tabs comprise from 4 to 16 tabs distributed around the circumference of the nozzle, each flexible tab comprising a tooth that, with the ring in the operative position, presses into and penetrates an outer surface of the flexible pipe.

* * * * *